United States Patent [19]
Depreux et al.

[11] Patent Number: 5,591,775
[45] Date of Patent: Jan. 7, 1997

[54] TRISUBSTITUTED NAPHTHYLALKYLAMIDES FOR DISORDERS OF THE MELATONINERGIC SYSTEM

[75] Inventors: Patrick Depreux, Armentieres; Hamid A. Mansour, Roubaix; Daniel Lesieur, Gondecourt; François Lefoulon, Orleans; Pierre Renard, Versailles; Gérard Adam, Le Mesnil Le Roi; Philippe Delagrange, Issy Les Moulineaux, all of France

[73] Assignee: Adir et Compagnie, Courbevoie, France

[21] Appl. No.: 349,914

[22] Filed: Dec. 6, 1994

[30] Foreign Application Priority Data

Dec. 7, 1993 [FR] France .................. 93 14630

[51] Int. Cl.⁶ .................... A61K 31/16; A61K 31/17; C07C 335/06; C07C 275/06
[52] U.S. Cl. .................. 514/580; 514/595; 514/599; 514/617; 564/26; 564/47; 564/74; 564/189; 564/190; 564/192; 564/209
[58] Field of Search .................. 514/580, 588, 514/613, 599, 595, 617; 564/17, 57, 58, 189, 190, 192, 209

[56] References Cited
FOREIGN PATENT DOCUMENTS

| | | |
|---|---|---|
| 0447285A1 | 9/1991 | European Pat. Off. . |
| 530087 | 3/1993 | European Pat. Off. . |
| 0562956A1 | 9/1993 | European Pat. Off. . |
| 3828566A1 | 3/1990 | Germany . |
| WO89/01472 | 2/1989 | WIPO . |

OTHER PUBLICATIONS

Yous et al., J. Med. Chem. 35(8), pp. 1484–1486 (1992).
CAS Abstract of published German Patent Application DE3828566, 1990.
Derwent Abstract of published German Patent Application DE3828566, 1990.
J. Med. Chem. 35, pp. 1484–1486 (1992).
Moritoki H. et al., Eur. J. Pharmacol. 35, pp. 185–198 (1976).
Morgan P. Journal of Neuroendocrinology 1, pp. 1–4 (1989).

*Primary Examiner*—Marianne M. Cintins
*Assistant Examiner*—Phyllis G. Spivack
*Attorney, Agent, or Firm*—The Firm of Gordon W. Hueschen

[57] ABSTRACT

The invention relates to a compound selected from those of formula (I):

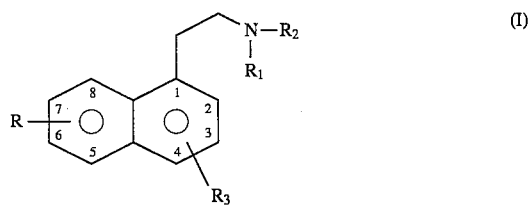

in which R, $R_1$, $R_2$ and $R_3$ are as defined herein for use in the treatment of a disorder of the melatoninergic system.

17 Claims, No Drawings

TRISUBSTITUTED NAPHTHYLALKYLAMIDES FOR DISORDERS OF THE MELATONINERGIC SYSTEM

The present invention relates to novel derivatives of naphthalene structure, the process for their preparation and the pharmaceutical compositions which contain them.

Patent EP 447,285 describes naphthalene derivatives which are monosubstituted on the ring bearing the alkylamide chain. Patent Application EP 530,087 describes naphthylalkylurea and naphthylalkylthiourea derivatives which are also monosubstituted on the ring bearing the alkylurea chain. These compounds possess many advantageous pharmacological activities as a result of their affinity for melatonin receptors. Patent Application EP 562,956 describes naphthalene derivatives, monosubstituted on the ring bearing the alkylamide chain, which exhibit an antagonist nature toward melatonin. Document DE 3,828,566 describes 1-acetyl-4-(2-acetylaminoethyl)naphthalene, but exclusively as a synthesis intermediate.

Besides their beneficial action on circadian rhythm disorders (J. Neurosurg. (63), Sept. 1985, page 333) and on sleeping disorders (Psychopharmacology, 1990, 100, page 222), compounds acting on the melatoninergic system possess advantageous pharmacological properties on the central nervous system, in particular anxiolytic properties (Neuropharmacology of Pineal Secretions, vol. 8, No.3–4, 1990, page 272), antipsychotic properties (Neuropharmacology of Pineal Secretions, vol. 8, No.3–4, 1990, page 267), analgesic properties (Pharmacopsychiat., 20, 1987, page 222), for the treatment of Parkinson's disease (J. Neurosurg. (63), Sept. 1985, page 331) and for Alzheimer's disease (Brain Research, 528, 1990, page 173). Likewise, these compounds have shown an activity on some cancers (Melatonin - Clinical Perspectives, 1988, page 164–165), on ovulation (Science, vol. 227, page 719–720), on immunomodulation (Adv. Pineal Research, vol. 5, 1991) and on diabetes (Clinical endocrinology, 24, 1986, page 363).

The Applicant has discovered novel naphthalene derivatives, disubstituted on the ring bearing the alkylamide chain, which are powerful ligands for the melatonin receptors.

More particularly, the invention relates to the compounds of formula (I):

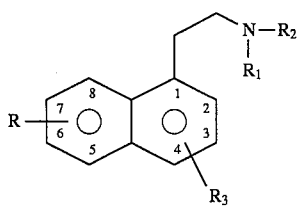

in which:

R represents a hydrogen or a radical chosen from alkyl, substituted alkyl and —O—R'; with R' representing a hydrogen or an alkyl, substituted alkyl, cycloalkyl, substituted cycloalkyl, cycloalkylalkyl, substituted cycloalkylalkyl, phenyl, substituted phenyl, phenylalkyl, substituted phenylalkyl, diphenylalkyl or substituted diphenylalkyl radical;

$R_1$ represents a hydrogen or an alkyl;

$R_2$ means a)

in which $X^1$ represents a sulfur or oxygen atom and $R_{40}$ represents a hydrogen or a radical chosen from alkyl, substituted alkyl, cycloalkyl, substituted cycloalkyl, cycloalkylalkyl, substituted cycloalkylalkyl, alkenyl, substituted alkenyl, alkynyl and substituted alkynyl; or b)

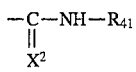

in which $X^2$ represents a sulfur or an oxygen and $R_{41}$ represents a hydrogen or a radical chosen from alkyl, cycloalkyl and cycloalkylalkyl;

$R_3$ represents a radical chosen from:
 $(C_2-C_6)$ alkyl,
 substituted $(C_2-C_6)$ alkyl,
 cycloalkylalkyl,
 substituted cycloalkylalkyl,
 alkenyl,
 substituted alkenyl,
 alkynyl,
 substituted alkynyl,
 hydroxyl in 3-position,
 $R_5$-alkyl-, with $R_5$ being substituted or unsubstituted and representing a radical chosen from pyridyl, phenyl, naphthyl, thienyl, furyl, pyrimidyl, indolyl, benzofuryl, benzothienyl, quinolyl and isoquinolyl;
 $R_6$—CO—O—,
 and $R_6$—CO—, with $R_6$ representing a radical chosen from $(C_1-C_5)$alkyl, substituted $(C_1-C_5)$alkyl, cycloalkyl, substituted cycloalkyl, cycloalkyl$(C_1-C_5)$alkyl, substituted cycloalkyl$(C_1-C_5)$alkyle, $R_5$- and $R_5$-alkyl- where $R_5$, being unsubstituted or substituted, is as defined above, it being understood that the compound of formula (I) cannot be N-{2-[(4-acetyl)naphth-1-yl]ethyl}acetamide, the terms "alkyl" and "alkoxy" denoting, except where otherwise mentioned, linear or branched groups of 1 to 6 carbon atoms, the terms "alkenyl" and "alkynyl" denoting unsaturated, linear or branched groups of 2 to 6 carbon atoms, the term "cycloalkyl" denoting a cyclic group of 3 to 8 carbon atoms, the term "substituted" applied to "alkyl", "alkoxy", "alkenyl", "alkynyl", "cycloalkyl" or "cycloalkylalkyl" means that these groups are substituted with one or more radicals chosen from alkyl, alkoxy and halogen;

the term "substituted" associated with $R_5$ and with "phenyl", "phenylalkyl" or "diphenylalkyl" means that these groups are substituted with one or more radicals chosen from alkyl, alkoxy, halogen, hydroxyl and trifluoromethyl;

their enantiomers and diastereoisomers, and their addition salts with a pharmaceutically acceptable acid or base.

The invention relates, for example, to the compounds of formula (I) in which:

$R_3$ is attached to position 3 of the naphthalene ring $R_3$ is a hydroxyl, $R_3$ is a $(C_2-C_6)$alkyl, $R_3$ is a cycloalkylalkyl, $R_3$ is a group $R_5$-alkyl-, $R_3$ is a group $R_5$-alkyl- in which $R_5$ is a phenyl, $R_3$ is a group $R_6$—CO—O—, $R_3$ is a group $R_6$—CO—, $R_6$ is a ($C_1$–$C_5$) alkyl, $R_6$ is a cycloalkyl, $R_6$ is a cycloalkylalkyl, $R_6$ is a phenyl, R is attached to position 7 of the naphthalene ring, R is a hydrogen, R is a hydroxyl, R is an alkyl, R is an alkoxy, $R_1$ is a hydrogen, $R_2$ is a group —CO—$R_{40}$, $R_2$ is a group —CS—$R_{40}$, $R_{40}$ is an alkyl, $R_{40}$ is a cycloalkyl, $R_{40}$ is an alkenyl, $R_2$ is a group —CX—NH—$R_{41}$, X is an oxygen, X is a sulfur, $R_{41}$ is an alkyl, or $R_{41}$ is a cycloalkyl.

The invention preferably relates to the following compounds:

N-[2-(7-methoxy-3-benzoylnaphth-1-yl)ethyl]-acetamide,

N-[2-(7-methoxy-3-cyclopropylcarbonylnaphth-1-yl)-ethyl]acetamide,

N-[2-(7-methoxy-3-propionylnaphth-1-yl)ethyl]-acetamide,

N-[2-(7-methoxy-3-acetylnaphth-1-yl)ethyl]acetamide,

N-[2-(7-methoxy-3-acetylnaphth-1-yl)ethyl]cyclopropyl-carboxamide,

N-[2-(7-methoxy-3-hydroxynaphth-1-yl)ethyl]-acetamide,

N-[2-(3,7-dihydroxynaphth-1-yl)ethyl]carboxamide,

N-[2-(7-methoxy-3-benzylnaphth-1-yl)ethyl]acetamide,

N-[2-(7-methoxy-3-ethylnaphth-1-yl)ethyl]acetamide,

N-[2-(7-methoxy-3-cyclopropylmethylnaphth-1-yl)-ethyl]acetamide,

N-[2-(7-methoxy-3-propylnaphth-1-yl)ethyl]acetamide,

N-[2-(7-methoxy-3-ethylnaphth-1-yl)ethyl]cyclopropyl-carboxamide.

Among the pharmaceutically acceptable acids which may be used to form an addition salt with the compounds of the invention, there may be mentioned by way of examples and with no limitation being implied, hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

Similarly, among the pharmaceutically acceptable bases which may be used to form an addition salt, there may be mentioned sodium hydroxide, potassium hydroxide, calcium hydroxide or aluminum hydroxide, alkali metal carbonates or alkaline-earth metal carbonates, and organic bases such as triethylamine, benzylamine, diethanolamine, tert-butylamine, dicyclohexylamine and arginine.

In particular, the alkyl radicals present in the formula (I) may be chosen from methyl, ethyl, n-propyl, isopropyl, n-butyl, isobutyl, sec-butyl, tert-butyl, pentyl and hexyl.

The alkoxy radicals present in the formula (I) may be chosen from methoxy, ethoxy, n-propoxy, isopropoxy, n-butoxy, iso-butoxy, tert-butoxy, pentyloxy and hexyloxy.

The halogens present in the formula (I) may be chosen from chlorine, bromine, iodine or fluorin. The cycloalkyl radicals present in the formula (I) may be chosen from cyclopropyl, cyclobutyl, cyclopentyl, cyclohexyl, cycloheptyl and cyclooctyl.

The invention also covers the process for the preparation of the compounds of formula (I), in which a compound of formula (II):

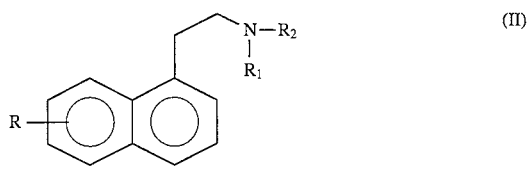

in which R, $R_1$ and $R_2$ are as defined in the formula (I), is reacted with a compound of formula (III):

in which $R_6$ is as defined in the formula (I), in order to obtain a corresponding compound of formula (Ia):

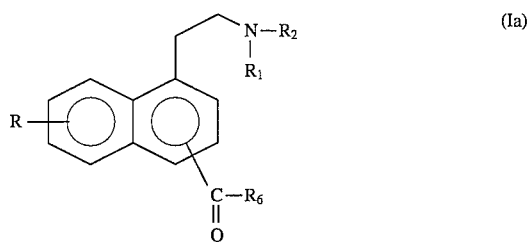

in which R, $R_1$, $R_2$ and $R_6$ are as defined above, which may be, if so desired, either subjected to an oxidation by a Baeyer-Villiger reaction, in order to obtain a corresponding compound of formula (Ib):

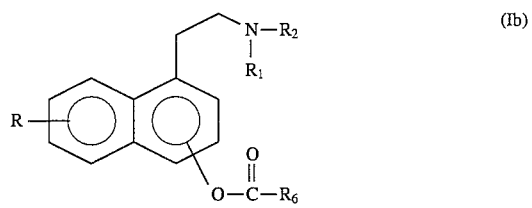

in which R, $R_1$, $R_2$ and $R_6$ are as defined above, and then if the —O—CO—$R_6$ substituent is in 3-position subjected to a saponification in the presence of sodium hydroxide, in order to obtain a corresponding compound of formula (Ic):

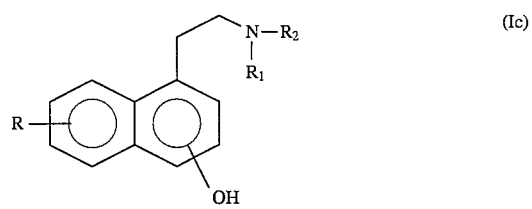

in which R, $R_1$ and $R_2$ are as defined above, or subjected to a reduction by mercury and zinc, in the presence of toluene and hydrochloric acid, in order to obtain a corresponding compound of formula (Id):

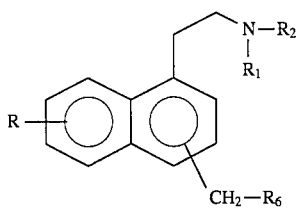

in which R, $R_1$, $R_2$ and $R_6$ are as defined above,
the compounds of formula (Ia), (Ib), (Ic) and (Id) forming the set of compounds of formula (I),
which compounds of formula (I) may be,
  purified according to one or more purification methods chosen from crystallization, chromatography on silica gel, extraction, filtration, and passage on charcoal or resin,
  separated, where appropriate, in pure form or in the form of a mixture, into their possible enantiomers or diastereoisomers,
  or salified by a pharmaceutically acceptable acid or base.

More particularly, the invention relates to the process for the preparation of the compounds of formula (I'), a particular case of the compounds of formula (I) in which $R_3$ is in the 3-position of naphthalene, in which a compound of formula (II):

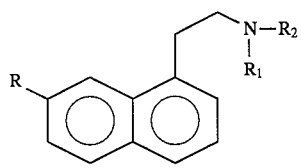

in which R, $R_1$ and $R_2$ are as defined in the formula (I), is reacted with a compound of formula (III):

$R_6$—COCl  (III)

in which $R_6$ is as defined in the formula (I),
in order to obtain a corresponding compound of formula (Ia'):

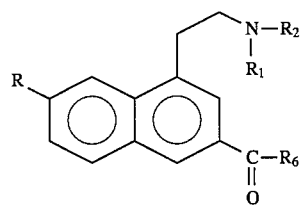

in which R, $R_1$, $R_2$ and $R_6$ are defined as above,
which may be, if so desired,
  either subjected to an oxidation by a Baeyer-Villiger reaction, in order to obtain a corresponding compound of general formula (Ib'):
in which R, $R_1$, $R_2$ and $R_6$ are as defined above, and then optionally

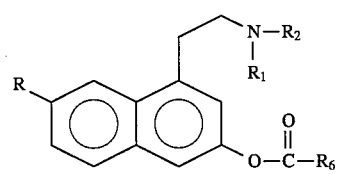

subjected to a saponification in the presence of sodium hydroxide, in order to obtain a corresponding compound of formula (Ic'):

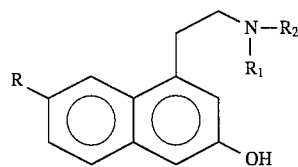

in which R, $R_1$ and $R_2$ are as defined above,
  or subjected to a reduction by mercury and zinc, in the presence of toluene and hydrochloric acid, in order to obtain a corresponding compound of formula (Id'):

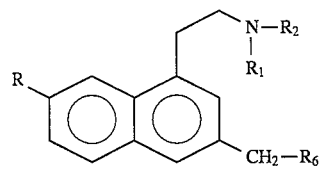

in which R, $R_1$, $R_2$ and $R_6$ are as defined above,
the compounds of formula (Ia'), (Ib'), (Ic') and (Id') forming the set of compounds of formula (I'),
which compounds of formula (I') may be, if so desired,
  purified according to one or more purification methods chosen from crystallization, chromatography on silica gel, extraction, filtration, and passage on charcoal or resin,
  separated, where appropriate, in pure form or in the form of a mixture, into their possible enantiomers or diastereoisomers,
  or salified by a pharmaceutically acceptable acid or base.

The compounds of formula (Ia), (Ib), (Ic) and (Id) may also, if R represents —OCH$_3$, be subjected to a demethylation reaction by boron tribromide. More particularly, the compounds of formula (Ia'), (Ib'), (Ic') and (Id') may, if R represents —OCH$_3$, be subjected to a demethylation reaction by boron tribromide. The corresponding hydroxylated compounds obtained also form part of the compounds of formula (I) according to the invention.

The starting materials used in the process described above are either commercially available or readily accessible to a person skilled in the art, according to processes which are well known in the literature. Reference will more particularly be made, for the compounds of general formula (II), to the descriptions of Patent EP 447,285 and Patent Application EP 530,087.

The thiocarboxamide compounds are readily obtained by a person skilled in the art, in particular by the use of Lawesson's reagent.

The compounds of formula (I) possess very advantageous pharmacological properties and are useful for the treatment of melatoninergic disorders.

The pharmacological study of the derivatives of the invention has, in fact, shown that they were not toxic and were endowed with a very high selective affinity for the melatonin receptors and with considerable activity on the central nervous system, and beneficial properties were noticed in particular toward sleeping disorders, anxiolytic, antipsychotic and analgesic properties as well as advantageous properties on microcirculation which make it possible to establish that the products of the invention are useful in the treatment of stress, sleeping disorders, anxiety, seasonal depressions, insomnia and tiredness due to jet lag, schizophrenia, panic attacks, melancholia, appetite regulation, psychotic disorders, epilepsy, Parkinson's disease, senile dementia, various disorders associated with normal or pathological ageing, migraine, memory loss and Alzheimer's diseases, as well as cerebral circulatory disorders. In another field of activity, it appears that the products of the invention possess properties as ovulation inhibitors and immunomodulators, and that they are capable of being used in the treatment of certain hormone-dependent cancers.

The compounds will preferably be used in the treatment of seasonal depression, sleeping disorders, cardiovascular pathologies, insomnia and tiredness due to time zone changes, and in appetite disorders and obesity.

For example, the compounds will be used in the treatment of seasonal depressions and sleeping disorders.

The compounds of the invention also possess a very advantageous metabolic profile.

Another subject of the present invention is the pharmaceutical compositions containing a compound of formula (I) or, where appropriate, one of its addition salts with a pharmaceutically acceptable acid or base in combination with one or more pharmaceutically acceptable excipients.

Among the pharmaceutical compositions according to the invention, mention may more particularly be made of those which are suitable for oral, parenteral, nasal, percutaneous or transcutaneous, rectal, perlingual, ocular or respiratory administration and in particular simple or sugar-coated tablets, sublingual tablets, sachets, packets, gelatin capsules, glossettes, pills, suppositories, creams, ointments, dermal gels, and drinkable or injectable ampules.

The dosage varies depending on the age and weight of the patient, the route of administration, the nature of the therapeutic indication, or possible treatments which may be associated, and increases in graduated doses between 0.1 mg and 1 g taken once or twice per 24 hours, more particularly 1 to 100 mg, for example 1 to 10 mg.

The examples which follow illustrate the invention but in no way imply any limitation thereof.

EXAMPLE 1:

N-[2-(7-METHOXY-3-BENZOYLNAPHTH-1-YL)-ETHYL]-ACETAMIDE

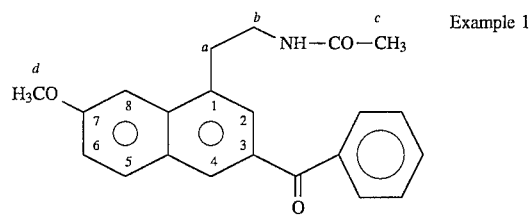

Example 1

To a solution of 11 g (45.2 mmol) of N-[2-(7-methoxynaphth-1-yl)ethyl]acetamide and 7.7 g (57.7 mmol) of $AlCl_3$ in 60 $cm^3$ of nitrobenzene, add dropwise 57.9 mmol of benzoyl chloride, at 12° C. and under nitrogen. Allow to react for 2 hours at 12° C. and pour the reaction mixture onto ice. Extract with dichloromethane, dry over magnesium sulfate, concentrate and then chromatograph the crude material on silica (eluent $CH_2Cl_2/CH_3OH$: 99/1).

The compound of Example 1 is obtained:

Yield: 34% Melting point: 92°–95° C. Recrystallization solvent : Toluene/hexane Molecular weight: 365.411 for $C_{22}H_{21}NO_3$; $1H_2O$

| | Microanalysis: | |
|---|---|---|
| | C % | H % |
| Calculated | 72.30 | 6.34 |
| Found | 72.55 | 6.30 |

Infra-red: $\nu$N—H (amide): 3340 $cm^{-1}$ $\nu$C=O (ketone): 1660 $cm^{-1}$ $\nu$C=O (amide): 1625 $cm^{-1}$ NMR (DMSO-$d_6$) 300 MHz 1.84 ppm (singlet, 3H, (Hc)) 3.23 ppm ( triplet, 2H, (Ha)) 3.37 ppm (quartet, 2H, (Hb)) 4.00 ppm (singlet, 3H, (Hd)) 7.28 ppm (doublet, 1H, ($H_6$), $J_{6-5}$=9 Hz) 7.57–7.81 ppm (unresolved complex, 7H, [$H_2$, $H_4$, H(A)]) 8.00 ppm (doublet, 1H, (H5), $J_{5-6}$=9 Hz) 8.14 ppm (multiplet, 2H, ($H_8$, NH))

EXAMPLES 2 TO 15

By working as in Example 1 but replacing N-[2-(7-methoxynaphth-1-yl)ethyl]acetamide by the compound suitably substituted on the amide function, the compounds of the following examples are obtained:

EXAMPLE 2:

N-[2-(7-METHOXY-3-BENZOYLNAPHTH-1-YL)-ETHYL]PROPIONAMIDE

EXAMPLE 3:

N-[2-(7-METHOXY-3-BENZOYLNAPHTH-1-YL)-ETHYL]BUTYRAMIDE

EXAMPLE 4:

N-[2-(7-METHOXY-3-BENZOYLNAPHTH-1-YL)-ETHYL]PENTANAMIDE

EXAMPLE 5:

N-[2-(7-METHOXY-3-BENZOYLNAPHTH-1-YL)-ETHYL]HEXANAMIDE

EXAMPLE 6:

N-[2-(7-METHOXY-3-BENZOYLNAPHTH-1-YL)-ETHYL]CYCLOPROPYLCARBOXAMIDE

EXAMPLE 7:

N-[2-(7-METHOXY-3-BENZOYLNAPHTH-1-YL)-ETHYL]CYCLOBUTYLCARBOXAMIDE

EXAMPLE 8:

N-[2-(7-METHOXY-3-BENZOYLNAPHTH-1-YL)-ETHYL]CYCLOPENTYLCARBOXAMIDE

EXAMPLE 9:

N-[2-(7-METHOXY-3-BENZOYLNAPHTH-1-YL)-ETHYL]CYCLOHEXYLCARBOXAMIDE

EXAMPLE 10:

N-[2-(7-METHOXY-3-BENZOYLNAPHTH-1-YL)-ETHYL]-N'-METHYLUREA

EXAMPLE 11:

N-[2-(7-METHOXY-3-BENZOYLNAPHTH-1-YL)-ETHYL]-N'-ETHYLUREA

EXAMPLE 12:

N-[2-(7-METHOXY-3-BENZOYLNAPHTH-1-YL)-ETHYL]-N'-PROPYLUREA

EXAMPLE 13:

N-[2-(7-METHOXY-3-BENZOYLNAPHTH-1-YL)-ETHYL]-N'-HEXYLUREA

EXAMPLE 14:

N-[2-(7-METHOXY-3-BENZOYLNAPHTH-1-YL)-ETHYL]-N'-CYCLOPROPYLUREA

EXAMPLE 15:

N-[2-(7-METHOXY-3-BENZOYLNAPHTH-1-YL)-ETHYL]-N'-CYCLOHEXYLUREA

EXAMPLES 16 TO 26

By working as in Example 1, but replacing N-[2-(7-methoxynaphth-1-yl)ethyl]acetamide by the compound suitably substituted in the 7-position of naphthalene and also, where appropriate, suitably substituted on the amide function, the compounds of the following examples are obtained:

EXAMPLE 16:

N-[2-(3-BENZOYLNAPHTH-1-YL)ETHYL]ACETAMIDE

EXAMPLE 16 bis:

N-[2-(7-ETHOXY-3-BENZOYLNAPHTH-1-YL)-ETHYL]ACETAMIDE

EXAMPLE 17:

N-[2-(7-PROPOXY-3-BENZOYLNAPHTH-1-YL)-ETHYL]ACETAMIDE

EXAMPLE 18:

N-[2-(7-PENTOXY-3-BENZOYLNAPHTH-1l-YL)-ETHYL]ACETAMIDE

EXAMPLE 19:

N-[2-(7-ALLYLOXY-3-BENZOYLNAPHTH-1-YL)ETHYL]ACETAMIDE

EXAMPLE 20:

N-[2-(7-PROPARGYLOXY-3-BENZOYL-NAPHTH-1-YL)ETHYL]ACETAMIDE

EXAMPLE 21:

N-[2-(7-CYCLOPROPYLMETHYLOXY-3-BENZOYLNAPHTH-1-YL)ETHYL]ACETAMIDE

EXAMPLE 22:

N-[2-(7-CYCLOHEXYLOXY-3-BENZOYL-NAPHTH-1-YL)ETHYL]ACETAMIDE

EXAMPLE 23:

N-[2-(7-CYCLOHEXEN-2-YLOXY-3-BENZOYL-NAPHTH-1-YL)ETHYL]ACETAMIDE

EXAMPLE 24:

N-[2-(7-BENZYLOXY-3-BENZOYLNAPHTH-1-YL)ETHYL]ACETAMIDE

EXAMPLE 25:

N-[2-(3-BENZOYLNAPHTH-1-YL)ETHYL]CYCLOPROPYLCARBOXAMIDE

EXAMPLE 26:

N-[2-(3-BENZOYLNAPHTH-1-YL)ETHYL]CY-CLOBUTYLCARBOXAMIDE

EXAMPLE 27:

N-[2-(7-METHOXY-3-CYCLOPROPYLCARBON-YLNAPHTH-1-YL)ETHYL]ACETAMIDE

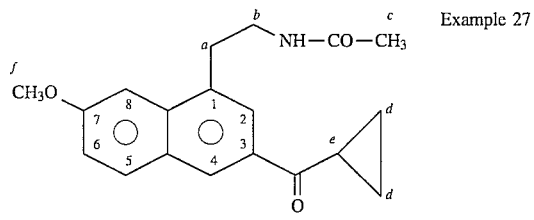

Example 27

By working in the same way as in Example 1, but using cyclopropanecarboxylic acid chloride for the acylation reaction, the compound of Example 27 is obtained:

Yield: 29% Recrystallization solvent: cyclohexane Melting point: 152° C. Molecular weight: 309.349 for $C_{19}H_{19}NO_3$

|  | Microanalysis: | | |
| --- | --- | --- | --- |
|  | C % | H % | N % |
| Calculated | 73.28 | 6.79 | 4.49 |
| Found | 73.00 | 6.83 | 4.38 |

Infra-red: $\nu$N—H (amide): 3340 cm$^{-1}$ $\nu$C=O (ketone): 1660 cm$^{-1}$ $\nu$C=O (amide): 1630 cm$^{-1}$ NMR (DMSO-$d_6$) 1.05 ppm (doublet, 4H, ($H_d$)) 1.80 ppm (singlet, 3H, ($H_c$)) 3.05 ppm (triplet, 1H, ($H_e$)) 3.20 ppm (triplet, 2H, ($H_a$)) 3.35 ppm (multiplet, 2H, ($H_b$)) 4.00 ppm (singlet, 3H, ($H_f$)) 7.30 ppm (doublet, 1H, ($H_6$) $J_{5-6}$=8.80 Hz) 7.70 ppm (singlet, 1H, ($H_8$)) 7.85 ppm (singlet, 1H, ($H_2$ or $H_4$)) 8.05 ppm (doublet, 1H, ($H_5$) $J_{5-6}$=8.80 Hz) 8.13 ppm (signal, 1H, NH) 8.65 ppm (singlet, 1H ($H_4$ or $H_2$))

EXAMPLES 28 TO 33

By working as in Example 27, but replacing N-[2-(7-methoxynaphth-1-yl)ethyl]acetamide by the compound suitably substituted on the amide function, the compounds of the following examples are obtained:

EXAMPLE 28:

N-[2-(7-METHOXY-3-CYCLOPROPYLCARBO-NYL NAPHTH-1-YL)ETHYL]PROPIONA-MIDE

EXAMPLE 29:

N-[2-(7-METHOXY-3-CYCLOPROPYLCARBO-NYL NAPHTH-1-YL)ETHYL]BUTYRA-MIDE

EXAMPLE 30:

N-[2-(7-METHOXY-3-CYCLOPROPYLCARBO-NYL NAPHTH-1-YL)ETHYL]CYCLOPRO-PYLCARBOXAMIDE

EXAMPLE 31:

N-[2-(7-METHOXY-3-CYCLOPROPYLCARBO-NYL NAPHTH-1-YL)ETHYL]CYCLOBU-TYLCARBOXAMIDE

EXAMPLE 32:

N-[2-(7-METHOXY-3-CYCLOPROPYLCARBO-NYL NAPHTH-1-YL)ETHYL]-N'-METHY-LUREA

EXAMPLE 33:

N-[2-(7-METHOXY-3-CYCLOPROPYLCARBO-NYL NAPHTH-1-YL)ETHYL]-N'-PROPY-LUREA

EXAMPLES 34 TO 37

By working as in Example 27, but replacing N-[2-(7-methoxynaphth-1-yl)ethyl]acetamide for the compound suitably substituted in the 7-position of naphthalene and, where appropriate, suitably substituted on the amide function, the compounds of the following examples are obtained:

EXAMPLE 34:

N-[2-(3-CYCLOPROPYLCARBONYLNAPHTH-1-YL)ETHYL]ACETAMIDE

EXAMPLE 35:

N-[2-(7-CYCLOPROPYLMETHYLOXY-3-CY-CLOPROPYLCARBONYLNAPHTH-1-YL)-ETHYL]ACETAMIDE

EXAMPLE 36:

N-[2-3-CYCLOPROPYLCARBONYLNAPHTH-1-YL)ETHYL]CYCLOPROPYLCARBOXAM-IDE

EXAMPLE 37:

N-[2(3-CYCLOPROPYLCARBONYL-NAPHTH-1-YL)ETHYL]CYCLOBUTYLCARBOXAM-IDE

EXAMPLE 38:

N-[2-(7-METHOXY-3-PROPIONYLNAPHTH-1-YL)ETHYL]ACETAMIDE

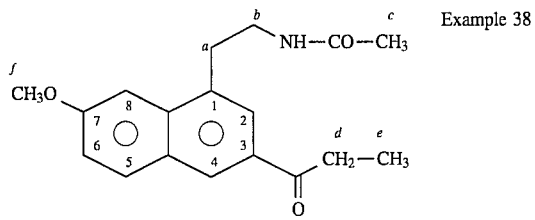

Example 38

By working in the same way as in Example 1, but using propionyl chloride for the acylation reaction, the compound of Example 38 is obtained:

Yield: 47% Recrystallization solvent: toluene Melting point: 141°–143° C. Molecular weight: 299.255 for $C_{18}H_{21}NO_3$

|  | Microanalysis: | | |
|---|---|---|---|
|  | C % | H % | N % |
| Calculated | 72.21 | 7.07 | 4.68 |
| Found | 72.51 | 6.99 | 4.52 |

Infra-red: $\nu$N—H (amide): 3380 cm$^{-1}$ $\nu$C=O (ketone): 1665 cm$^{-1}$ $\nu$C=O (amide): 1610 cm$^{-1}$ NMR (DMSO-$d_6$) 1.13 ppm ( triplet, 3H, ($H_e$)) 1.83 ppm (singlet, 3H, ($H_c$)) 3.15 ppm (multiplet, 4H, ($H_a$, $H_d$)) 3.32 ppm (multiplet, 2H, ($H_b$)) 4.00 ppm (singlet, 3H, (H)) 7.30 ppm (resolved doublet, 1H, ($H_6$) $J_{6-5}$=9.00 Hz, $J_{6-8}$=2.25 Hz) 7.70 ppm (doublet, 1H, ($H_8$) $J_{2-6}$=2.25 Hz) 7.80 ppm (singlet, 1H, ($H_2$ or $H_4$)) 8.00 ppm (doublet, 1H, ($H_5$) $J_{5-6}$=9.00 Hz)) 8.15 ppm (triplet, 1H, (NH)) 8.50 ppm (singlet, 1H, ($H_4$ or $H_2$))

EXAMPLES 39 TO 44

By working as in Example 38, but replacing N-[2-(7-methoxynaphth-1-yl)ethyl]acetamide by the compound suitably substituted on the amide function, the compounds of the following examples are obtained:

EXAMPLE 39:

N-[2-(7-METHOXY-3-PROPIONYLNAPHTH-1-YL)ETHYL]PROPIONAMIDE

EXAMPLE 40:

N-[2-(7-METHOXY-3-PROPIONYLNAPHTH-1-YL)ETHYL]BUTYRAMIDE

EXAMPLE 41:

N-[2-(7-METHOXY-3-PROPIONYLNAPHTH-1-YL)ETHYL]CYCLOPROPYLCARBOXAMIDE

EXAMPLE 42:

N-[2-(7-METHOXY-3-PROPIONYLNAPHTH-1-YL)ETHYL]CYCLOBUTYLCARBOXAMIDE

EXAMPLE 43:

N-[2-(7-METHOXY-3-PROPIONYLNAPHTH-1-YL)ETHYL]-N'-METHYLUREA

EXAMPLE 44:

N-[2-(7-METHOXY-3-PROPIONYLNAPHTH-1-YL)ETHYL]-N'-PROPYLUREA

EXAMPLES 45 TO 48

By working as in Example 38, but replacing N-[2-(7-methoxynaphth-1-yl)ethyl]acetamide by the compound suitably substituted in the 7-position of naphthalene and, where appropriate, suitably substituted on the amide function, the compounds of the following examples are obtained:

EXAMPLE 45:

N-[2-(3-PROPIONYLNAPHTH-1-YL)ETHYL] ACETAMIDE

EXAMPLE 46:

N-[2-(7-CYCLOPROPYLMETHYLOXY-3-PROPIONYLNAPHTH-1-YL)ETHYL]ACETAMIDE

EXAMPLE 47:

N-[2-(3-PROPIONYLNAPHTH-1-YL)ETHYL] CYCLOPROPYLCARBOXAMIDE

EXAMPLE 48:

N-[2-(3-PROPIONYLNAPHTH-1-YL)ETHYL] CYCLOBUTYLCARBOXAMIDE

EXAMPLE 49:

N-[2-(7-METHOXY-3-ACETYLNAPHTH-1-YL)-ETHYL]ACETAMIDE

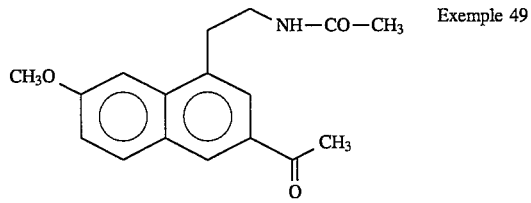

Exemple 49

By working as in Example 1, using acetyl chloride for the acylation reaction, the compound of Example 49 is obtained:

Molecular weight: 285.346 for $C_{17}H_{19}NO_3$ Melting point: 154.5° C.

| | Microanalysis: | | |
|---|---|---|---|
| | C % | H % | N % |
| Calculated | 71.56 | 6.71 | 4.91 |
| Found | 71.41 | 6.67 | 4.89 |

EXAMPLE 50:

N-[2-(7-METHOXY-3-ACETYLNAPHTH-1-YL)-ETHYL]CYCLOPROPYLCARBOXAMIDE

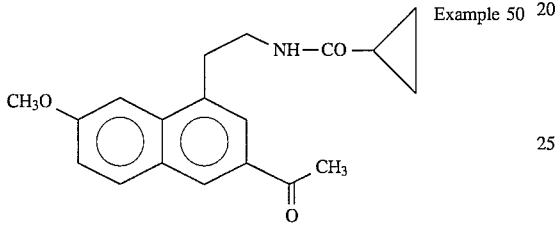

Example 50

By working as in Example 1, using N-[2-(7-methoxynaphth-1-yl)ethyl]cyclopropylcarboxamide and acetyl chloride as starting materials, the compound of Example 50 is obtained.

Yield: 31% Melting point: 140°–141° C. Recrystallization solvent: toluene Molecular weight: 311.365 for $C_{19}H_{21}NO_3$

| | Microanalysis: | | |
|---|---|---|---|
| | C % | H % | N % |
| Calculated | 73.28 | 6.79 | 4.49 |
| Found | 73.08 | 6.74 | 4.43 |

Infra-red: $\nu$N—H (amide): 3360 cm$^{-1}$ $\nu$C=O (ketone): 1680 cm$^{-1}$ $\nu$C=O (amide): 1600 cm$^{-1}$ NMR (DMSO=d$_6$) 0.65 ppm (multiplet, 4H, (H$_d$)) 2.65 ppm (singlet, 3H, (H$_c$)) 3.20 ppm (triplet, 2H, (H$_a$)) 3.40 ppm (multiplet, 2H, (H$_b$)) 4.00 ppm (singlet, 3H, (H$_f$)) 7.30 ppm (resolved doublet, 1H, (H$_6$) J$_{6\text{-}5}$=8.90 Hz, J$_{6\text{-}8}$=2.00 Hz) 7.60 ppm (doublet, 1H, (H$_8$) J$_{8\text{-}6}$=2.00 Hz) 7.80 ppm (singlet, 1H, (H$_2$ or H$_4$)) 8.00 ppm (doublet, 1H, (H$_5$) J$_{5\text{-}6}$=8.90 Hz) 8.30 ppm (triplet, 1H, (NH))

EXAMPLES 51 TO 63

Working as in Example 49, but replacing N-[2-(7-methoxynaphth-1-yl)ethyl]acetamide by the compound suitably substituted on the amide function, the compounds of the following examples are obtained:

EXAMPLE 51:

N-[2-(7-METHOXY-3-ACETYLNAPHTH-1-YL)-ETHYL]PROPIONAMIDE

EXAMPLE 52:

N-[2-(7-METHOXY-3-ACETYLNAPHTH-1-YL)-ETHYL]BUTYRAMIDE

EXAMPLE 53:

N-[2-(7-METHOXY-3-ACETYLNAPHTH-1-YL)-ETHYL]PENTANAMIDE

EXAMPLE 54:

N-[2-(7-METHOXY-3-ACETYLNAPHTH-1-YL)-ETHYL]HEXANAMIDE

EXAMPLE 55:

N-[2-(7-METHOXY-3-ACETYLNAPHTH-1-YL)-ETHYL]CYCLOBUTYLCARBOXAMIDE

EXAMPLE 56:

N-[2-(7-METHOXY-3-ACETYLNAPHTH-1-YL)-ETHYL]CYCLOPENTYLCARBOXAMIDE

EXAMPLE 57:

N-[2-(7-METHOXY-3-ACETYLNAPHTH-1-YL)-ETHYL]CYCLOHEXYLCARBOXAMIDE

EXAMPLE 58:

N-[2-(7-METHOXY-3-ACETYLNAPHTH-1-YL)-ETHYL]-N'-METHYLUREA

EXAMPLE 59:

N-[2-(7-METHOXY-3-ACETYLNAPHTH-1-YL)-ETHYL]-N'-ETHYLUREA

EXAMPLE 60:

N-[2-(7-METHOXY-3-ACETYLNAPHTH-1-YL)-ETHYL]-N'-PROPYLUREA

EXAMPLE 61:

N-[2-(7-METHOXY-3-ACETYLNAPHTH-1-YL)-ETHYL]-N'-HEXYLUREA

EXAMPLE 62:

N-[2-(7-METHOXY-3-ACETYLNAPHTH-1-YL)-ETHYL]-N'-CYCLOPROPYLUREA

EXAMPLE 63:

N-[2-(7-METHOXY-3-ACETYLNAPHTH-1-YL)-ETHYL]-N'-CYCLOHEXYLUREA

EXAMPLES 64 TO 75

By working as in Example 49, but replacing N-[2-(7-methoxynaphth-1-yl)ethyl]acetamide by the compound suitably substituted in the 7-position of naphthalene and also, where appropriate, suitably substituted on the amide function, the compounds of the following examples are obtained:

EXAMPLE 64:

N-[2-(3-ACETYLNAPHTH-1-YL)ETHYL]ACETAMIDE

EXAMPLE 65:

N-[2-(7-ETHOXY-3-ACETYLNAPHTH-1-YL)-ETHYL]ACETAMIDE

EXAMPLE 66:

N-[2-(7-PROPOXY-3-ACETYLNAPHTH-1-YL)-ETHYL]ACETAMIDE

EXAMPLE 67:

N-[2-(7-PENTOXY-3-ACETYLNAPHTH-1-YL)-ETHYL]ACETAMIDE

EXAMPLE 68:

N-[2-(7-ALLYLOXY-3-ACETYLNAPHTH-1-YL)-ETHYL]ACETAMIDE

EXAMPLE 69:

N-[2-(7-PROPARGYLOXY-3-ACETYLNAPHTH-1-YL)ETHYL]ACETAMIDE

EXAMPLE 70:

N-[2-(7-CYCLOPROPYLMETHYLOXY-3-ACETYLNAPHTH-1-YL)ETHYL]ACETAMIDE

EXAMPLE 71:

N-[2-(7-CYCLOHEXYLOXY-3-ACETYL-NAPHTH-1-YL)ETHYL]ACETAMIDE

EXAMPLE 72:

N-[2-(7-CYCLOHEXEN-2-YLOXY-3-ACETYL-NAPHTH-1-YL)ETHYL]ACETAMIDE

EXAMPLE 73:

N-[2-(7-BENZYLOXY-3-ACETYLNAPHTH-1-YL)ETHYL]ACETAMIDE

EXAMPLE 74:

N-[2-(3-ACETYLNAPHTH-1-YL)ETHYL]CYCLOPROPYLCARBOXAMIDE

EXAMPLE 75:

N-[2-(3-ACETYLNAPHTH-1-YL)ETHYL]CYCLOBUTYLCARBOXAMIDE

EXAMPLE 76:

N-[2-(7-METHOXY-3-ACETOXYNAPHTH-1-YL)ETHYL]ACETAMIDE

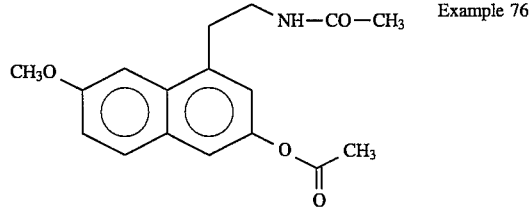

Example 76

To a solution of 2.8 g (9.81 mmol) of N-[2-(7-methoxy-3-acetylnaphth-1-yl)ethyl]acetamide, according to Example 49, in 125 cm$^3$ of methanol is added a solution of 7.6 g (12.3 mmol) of monoperoxyphthalic acid magnesium salt in 100 cm$^3$ of water adjusted to pH 5 with 1N NaOH. Stir at room temperature for 24 hours. Evaporate off the methanol, add 1N NaHCO$_3$, extract with CH$_2$Cl$_2$, dry over MgSO$_4$, filter and concentrate. The compound of Example 76 is obtained.

EXAMPLE 77:

N-[2-(7-METHOXY-3-HYDROXYNAPHTH-1-YL)ETHYL]ACETAMIDE

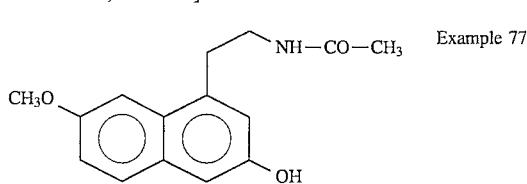
Example 77

EXAMPLE 77

Dissolve the residue obtained in Example 76, that is to say N-[2-(7-methoxy-3-acetoxynaphth-1-yl)ethyl]acetamide, in 200 cm³ of methanol and treat with 250 cm³ of 0.05N NaOH for 1 hour at room temperature. Evaporate off the MeOH, bring to pH 12 with 1N NaOH, extract with $CH_2Cl_2$, dry over $MgSO_4$, filter and concentrate. Chromatograph on silica eluting with $CH_2Cl_2$/MeOH : 98/2. 2.3 g (35%) of the compound of Example 77 are obtained.

Molecular weight: 259.307 Melting point: 154.8° C. Recrystallization solvent: $CH_2Cl_2$

| | Microanalysis: | | |
|---|---|---|---|
| | C % | H % | N % |
| Calculated | 69.48 | 6.61 | 5.40 |
| Found | 68.75 | 6.40 | 5.54 |

EXAMPLE 78:

N-[2-(3,7-DIHYDROXYNAPHTH-1-YL)ETHYL] ACETAMIDE

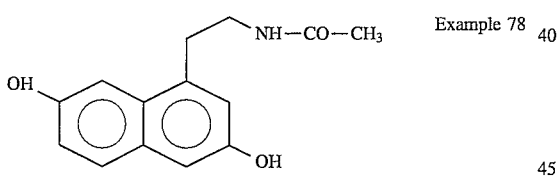
Example 78

Dissolve 0.2 g (0.771 mmol) of N-[2-(7-methoxy-3-hydroxynaphth-1-yl)ethyl]acetamide, according to Example 77, in 5 cm³ of anhydrous dichloromethane. Cool in a bath of ice and salt. Add dropwise 0.8 cm³ of 1M boron tribromide. Stir in ice at room temperature for 4 hours. Add a further 0.8 cm³ of 1M boron tribromide in $CH_2CL_2$. Allow to stir overnight at room temperature. Bring to pH 8 with 1N NaOH. Extract with $CH_2Cl_2$. Dry with $MgSO_4$. Evaporate off the solvent. Recover the product. Extract with methyl ethyl ketone. Dry over $MgSO_4$. Evaporate off the solvent. Purify the product on 30 g of silica. Elute with $CH_2Cl_2$/MeOH: 95/5. The product of Example 78 is obtained.

Molecular weight: 245.28 Melting point: 171°–175° C. Recrystallization solvents: $CH_3CN$, MeOH

EXAMPLES 79 TO 87

By working as in Examples 76 to 78, but using the suitably substituted naphthylalkylamide compound, the compounds of the following examples are obtained:

EXAMPLE 79:

N-[2-(7-METHOXY-3-ACETOXYNAPHTH-1-YL)ETHYL]PROPIONAMIDE

EXAMPLE 80:

N-[2-(7-METHOXY-3-HYDROXYNAPHTH-1-YL)ETHYL]PROPIONAMIDE

EXAMPLE 81:

N-[2-(3,7-DIHYDROXYNAPHTH-1-YL)ETHYL] PROPIONAMIDE

EXAMPLE 82:

N-[2-(7-METHOXY-3-ACETOXYNAPHTH-1-YL)ETHYL]CYCLOPROPYLCARBOXAMIDE

EXAMPLE 83:

N-[2-(7-METHOXY-3-HYDROXYNAPHTH-1-YL)ETHYL]CYCLOPROPYLCARBOXAMIDE

EXAMPLE 84:

N-[2-(3,7-DIHYDROXYNAPHTH-1-YL)ETHYL] CYCLOPROPYLCARBOXAMIDE

EXAMPLE 85:

N-[2-(7-METHOXY-3-ACETOXYNAPHTH-1-YL)ETHYL]CYCLOBUTYLCARBOXAMIDE

EXAMPLE 86:

N-[2-(7-METHOXY-3-HYDROXYNAPHTH-1-YL)ETHYL]CYCLOBUTYLCARBOXAMIDE

EXAMPLE 87:

N-[2-(3,7-DIHYDROXYNAPHTH-1-YL)ETHYL] CYCLOBUTYLCARBOXAMIDE

EXAMPLE 88:

N-[2-(7-METHOXY-3-BENZYLNAPHTH-1-YL)-ETHYL]ACETAMIDE

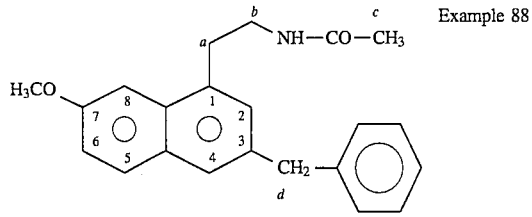

Example 88

A solution of 72 mg of mercuric chloride in 5.5 cm$^3$ of water is added to 3.6 g of zinc powder. Stir for 30 minutes. Allow to decant and remove the water.

Next, add 3.6 cm$^3$ of water to this amalgam, then 3.6 cm$^3$ of concentrated hydrochloric acid and then 5.26 mmol of N-[2-(7-methoxy-3-benzoylnaphth-1-yl)ethyl]acetamide, prepared according to Example 1, and 25 cm$^3$ of toluene.

Bring to reflux for 2 hours, extract the organic phase, wash with water, dry over magnesium sulfate, filter and evaporate to dryness.

The compound of Example 88 is obtained.

Yield: 35% Melting point: 85°–87° C. Recrystallization solvent: toluene Molecular weight: 333.411 for $C_{22}H_{23}NO_2$

|  | Microanalysis: | | |
| --- | --- | --- | --- |
|  | C % | H % | N % |
| Calculated | 79.24 | 6.95 | 4.20 |
| Found | 78.93 | 6.94 | 4.22 |

Infra-red: $\nu$N—H (amide): 3220 cm$^{-1}$ $\nu$C=O (amide): 1610 cm$^{-1}$ $\nu$C=O (aromatic): 1590 cm$^{-1}$ NMR (DMSO-$d_6$) 1.80 ppm (singlet, 3H, (H$_c$)) 3.00–3.45 ppm (unresolved complex, 4H, (H$_a$, H$_b$)) 3.90 ppm (singlet, 3H, (O CH$_3$)) 4.00 ppm (singlet, 2H, (H$_d$)) 7.00–7.80 ppm (unresolved complex, 10H, aromatic H) 8.00 ppm (signal, 1H, (NH))

EXAMPLES 89 TO 114

By working as in Example 88, but from the starting material of Examples 2 to 26, the compounds of the following examples are obtained:

EXAMPLE 89:

N-[2-(7-METHOXY-3-BENZYLNAPHTH-1-YL)-ETHYL]PROPIONAMIDE

EXAMPLE 90:

N-[2-(7-METHOXY-3-BENZYLNAPHTH-1-YL)-ETHYL]BUTYRAMIDE

EXAMPLE 91:

N-[2-(7-METHOXY-3-BENZYLNAPHTH-1-YL)-ETHYL]PENTANAMIDE

EXAMPLE 92:

N-[2-(7-METHOXY-3-BENZYLNAPHTH-1-YL)-ETHYL]HEXANAMIDE

EXAMPLE 93:

N-[2-(7-METHOXY-3-BENZYLNAPHTH-1-YL)-ETHYL]CYCLOPROPYLCARBOXAMIDE

EXAMPLE 94:

N-[2-(7-METHOXY-3-BENZYLNAPHTH-1-YL)-ETHYL]CYCLOBUTYLCARBOXAMIDE

EXAMPLE 95:

N-[2-(7-METHOXY-3-BENZYLNAPHTH-1-YL)-ETHYL]CYCLOPENTYLCARBOXAMIDE

EXAMPLE 96:

N-[2-(7-METHOXY-3-BENZYLNAPHTH-1-YL)-ETHYL]CYCLOHEXYLCARBOXAMIDE

EXAMPLE 97:

N-[2-(7-METHOXY-3-BENZYLNAPHTH-1-YL)-ETHYL]-N'-METHYLUREA

EXAMPLE 98:

N-[2-(7-METHOXY-3-BENZYLNAPHTH-1-YL)-ETHYL]-N'-ETHYLUREA

EXAMPLE 99:

N-[2-(7-METHOXY-3-BENZYLNAPHTH-1-YL)-ETHYL]-N'-PROPYLUREA

EXAMPLE 100:

N-[2-(7-METHOXY-3-BENZYLNAPHTH-1-YL)-ETHYL]-N'-HEXYLUREA

EXAMPLE 101:

N-[2-(7-METHOXY-3-BENZYLNAPHTH-1-YL)-ETHYL]-N'-CYCLOPROPYLUREA

EXAMPLE 102:

N-[2-(7-METHOXY-3-BENZYLNAPHTH-1-YL)-ETHYL]-N'-CYCLOHEXYLUREA

EXAMPLE 103:

N-[2-(3-BENZYLNAPHTH-1-YL)ETHYL]ACETAMIDE

EXAMPLE 104:

N-[2-(7-ETHOXY-3-BENZYLNAPHTH-1-YL)-ETHYL]ACETAMIDE

EXAMPLE 105:

N-[2-(7-PROPOXY-3-BENZYLNAPHTH-1-YL)-ETHYL]ACETAMIDE

EXAMPLE 106:

N-[2-(7-PENTOXY-3-BENZYLNAPHTH-1-YL)-ETHYL]ACETAMIDE

EXAMPLE 107:

N-[2-(7-ALLYLOXY-3-BENZYLNAPHTH-1-YL)-ETHYL]ACETAMIDE

EXAMPLE 108:

N-[2-(7-PROPARGYLOXY-3-BENZYLNAPHTH-1-YL)ETHYL]ACETAMIDE

EXAMPLE 109:

N-[2-(7-CYCLOPROPYLMETHYLOXY-3-BENZYLNAPHTH-1-YL)ETHYL]ACETAMIDE

EXAMPLE 110:

N-[2-(7-CYCLOHEXYLOXY-3l-BENZYL-NAPHTH-1-YL)ETHYL]ACETAMIDE

EXAMPLE 111:

N-[2-(7-CYCLOHEXEN-2-YLOXY-3-BENZYL-NAPHTH-1-YL)ETHYL]ACETAMIDE

EXAMPLE 112:

N-[2-(7-BENZYLOXY-3-BENZYLNAPHTH-1-YL)ETHYL]ACETAMIDE

EXAMPLE 113:

N-[2-(3-BENZYLNAPHTH-1-YL)ETHYL]CYCLOPROPYLCARBOXAMIDE

EXAMPLE 114:

N-[2(3-BENZYLNAPHTH-1-YL)ETHYL]CYCLOBUTYLCARBOXAMIDE

EXAMPLE 115:

N-[2-(7-METHOXY-3-ETHYLNAPHTH-1-YL)-ETHYL]ACETAMIDE

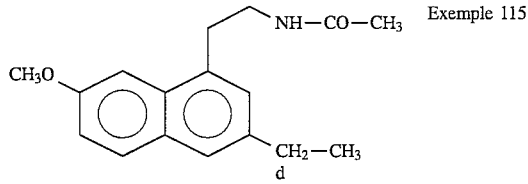

Exemple 115

Starting with N-[2-(7-methoxy-3-acetylnaphth-1-yl)ethyl]acetamide, prepared according to Example 49, and by working in the same way as in Example 88, the compound of Example 115 is obtained.

Molecular weight: 271.363 for $C_{17}H_{21}NO_2$ Melting point: 104°–105° C.

| | Microanalysis: | | |
|---|---|---|---|
| | C % | H % | N % |
| Calculated | 75.25 | 7.80 | 5.16 |
| Found | 74.99 | 8.12 | 5.08 |

EXAMPLES 116 TO 141

By working as in Example 115, but from the starting material of Examples 50 to 75, the compounds of the following examples are obtained:

EXAMPLE 116:

N-[2-(7-METHOXY-3-ETHYLNAPHTH-1-YL)-ETHYL]PROPIONAMIDE

EXAMPLE 117:

N-[2-(7-METHOXY-3-ETHYLNAPHTH-1-YL)-ETHYL]BUTYRAMIDE

EXAMPLE 118:

N-[2-(7-METHOXY-3-ETHYLNAPHTH-1-YL)-ETHYL]PENTANAMIDE

EXAMPLE 119:

N-[2-(7-METHOXY-3-ETHYLNAPHTH-1-YL)-ETHYL]HEXANAMIDE

EXAMPLE 120:

N-[2-(7-METHOXY-3-ETHYLNAPHTH-1-YL)-ETHYL]CYCLOPROPYLCARBOXAMIDE

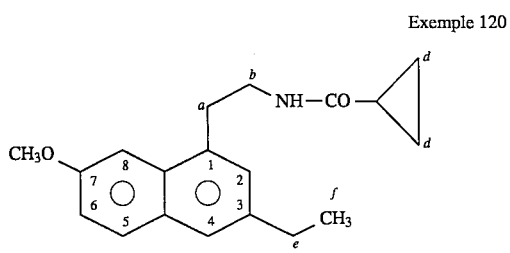

Exemple 120

Yield: 38% Melting point: 116°–118° C. Recrystallization solvent: cyclohexane Molecular weight: 297.381 for $C_{19}H_{23}NO_2$ Infra-red: $\nu$N—H (amide): 3240 cm$^{-1}$ $\nu$C=O (amide): 1620 cm$^{-1}$ NMR (DMSO-$d_6$) 0.70 ppm (multiplet, 4H, ($H_d$)) 1.25 ppm (triplet, 3H, ($H_f$)) 1.60 ppm (multiplet, 1H, ($H_c$)) 2.70 ppm (quartet, 2H, ($H_e$)) 3.10 ppm (triplet, 2H, ($H_a$)) 3.35 ppm (multiplet, 2H, ($H_b$)) 3.90 ppm (singlet, 3H, (OCH$_3$)) 7.10 ppm (doublet, 1H, ($H_6$), $J_{6-5}$=8.33 Hz) 7.15 ppm (singlet, 1H, ($H_8$)) 7.50 ppm (singlet, 2H, ($H_2$, $H_4$)) 7.70 ppm (doublet, 1H, ($H_5$), $J_{5-6}$=8.33 Hz)) 8.20 ppm (triplet, 1H, (NH))

EXAMPLE 121:

N-[2-(7-METHOXY-3-ETHYLNAPHTH-1-YL)-ETHYL]CYCLOBUTYLCARBOXAMIDE

EXAMPLE 122:

N-[2-(7-METHOXY-3-ETHYLNAPHTH-1-YL)-ETHYL]CYCLOPENTYLCARBOXAMIDE

EXAMPLE 123:

N-[2-(7-METHOXY-3-ETHYLNAPHTH-1-YL)-ETHYL]CYCLOHEXYLCARBOXAMIDE

EXAMPLE 124:

N-[2-(7-METHOXY-3-ETHYLNAPHTH-1-YL)-ETHYL]-N'-METHYLUREA

EXAMPLE 125:

N-[2-(7-METHOXY-3-ETHYLNAPHTH-1-YL)-ETHYL]-N'-ETHYLUREA

EXAMPLE 126:

N-[2-(7-METHOXY-3-ETHYLNAPHTH-1-YL)-ETHYL]-N'-PROPYLUREA

EXAMPLE 127:

N-[2-(7-METHOXY-3-ETHYLNAPHTH-1-YL)-ETHYL]-N'-HEXYLUREA

EXAMPLE 128:

N-[2-(7-METHOXY-3-ETHYLNAPHTH-1-YL)-ETHYL]-N'-CYCLOPROPYLUREA

EXAMPLE 129

N-[2-(7-METHOXY-3-ETHYLNAPHTH-1-YL)-ETHYL]-N'-CYCLOHEXYLUREA

EXAMPLE 130:

N-[2-(3-ETHYLNAPHTH-1-YL)ETHYL]ACETAMIDE

EXAMPLE 131:

N-[2-(7-ETHOXY-3-ETHYLNAPHTH-1-YL)-ETHYL]ACETAMIDE

EXAMPLE 132:

N-[2-(7-PROPOXY-3-ETHYLNAPHTH-1-YL)-ETHYL]ACETAMIDE

EXAMPLE 133:

N-[2-(7-PENTOXY-3-ETHYLNAPHTH-1-YL)-ETHYL]ACETAMIDE

EXAMPLE 134:

N-[2-(7-ALLYLOXY-3-ETHYLNAPHTH-1-YL)-ETHYL]ACETAMIDE

EXAMPLE 135:

N-[2-(7-PROPARGYLOXY-3-ETHYLNAPHTH-1-YL)ETHYL]ACETAMIDE

EXAMPLE 136:

N-[2-(7-CYCLOPROPYLMETHYLOXY-3-ETHYLNAPHTH-1-YL)ETHYL]ACETAMIDE

EXAMPLE 137:

N-[2-(7-CYCLOHEXYLOXY-3-ETHYLNAPHTH-1-YL)ETHYL]ACETAMIDE

EXAMPLE 138:

N-[2-(7-CYCLOHEXEN-2-YLOXY-3-ETHYL-NAPHTH-1-YL)ETHYL]ACETAMIDE

EXAMPLE 139:

N-[2-(7-BENZYLOXY-3-ETHYLNAPHTH-1-YL)-ETHYL]ACETAMIDE

EXAMPLE 140:

N-[2-(3-ETHYLNAPHTH-1-YL)ETHYL]CYCLO-PROPYLCARBOXAMIDE

EXAMPLE 141:

N-[2-(3-ETHYLNAPHTH-1-YL)ETHYL]CY-CLOBUTYLCARBOXAMIDE

EXAMPLE 142:

N-[2-(7-METHOXY-3-CYCLOPROPYLMETHYL-NAPHTH-1-YL)ETHYL]ACETAMIDE

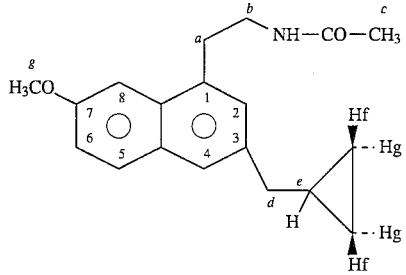

Starting with N-[2-(7-methoxy-3-cyclopropylcarbonyl-naphth-1-yl)ethyl]acetamide, prepared according to Example 27, and by working in the same way as in Example 88, the compound of Example 142 is obtained.

Yield: 37.5% Melting point 89°–90° C. Recrystallization solvent: cyclohexane Molecular weight: 301.885 for $C_{19}H_{23}NO_2 + \frac{1}{4} H_2O$

|  | Microanalysis: | | |
| --- | --- | --- | --- |
|  | C % | H % | N % |
| Calculated | 75.58 | 7.84 | 4.63 |
| Found | 75.65 | 7.74 | 4.49 |

Infra-red: $\nu$N—H (amide): 3240 cm$^{-1}$ $\nu$C=O (amide): 1625 cm$^{-1}$

NMR (DMSO-$d_6$) 0.20 ppm (multiplet, 2H, ($H_g$)) 0.50 ppm (multiplet, 2H, ($H_f$)) 1.05 ppm (multiplet, 1H, ($H_e$)) 1.85 ppm (singlet, 3H, ($H_c$)) 2.60 ppm (doublet, 2H, ($H_d$), J=6.84 Hz) 3.10 ppm (triplet, 2H, ($H_a$)) 3.30 ppm (multiplet, 2H, ($H_b$)) 3.90 ppm (singlet, 1H, (OCH$_3$)) 7.15 ppm (doubled doublet, 1H, ($H_6$), $J_{6-5}$=8.90 Hz, $J_{6-8}$=2.40 Hz) 7.25 ppm (singlet, 1H, ($H_8$), $J_{8-6}$=2.40 Hz) 7.55 ppm (multiplet, 2H, ($H_2$, $H_4$ Hz)) 7.80 ppm (doublet, 1H, ($H_5$), $J_{5-6}$=8.90 Hz) 8.10 ppm (triplet, 1H, (NH))

EXAMPLE 143:

N-[2-(7-METHOXY-3-PROPYLNAPHTH-1-YL)-ETHYL]ACETAMIDE

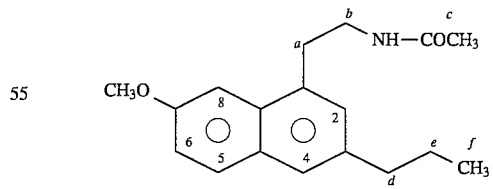

Starting with N-[2-(7-methoxy-3-propionylnaphth-1-yl)ethyl]acetamide, prepared according to Example 38, and by working in the same way as in Example 88, the compound of Example 143 is obtained.

Yield: 60% Melting point: 80°–82° C. Recrystallization solvent: petroleum ether Molecular weight: 285.371 for $C_{18}H_{23}NO_2$

|            | Microanalysis: |       |       |
|------------|----------------|-------|-------|
|            | C %            | H %   | N %   |
| Calculated | 75.75          | 8.12  | 4.91  |
| Found      | 75.46          | 7.95  | 4.90  |

Infra-red: νN—H (amide): 3230 cm$^{-1}$ νC=O (amide): 1620 cm$^{-1}$ νC=C (aromatic): 1600 cm$^{-1}$ NMR (DMSO-d$_6$) 0.90 ppm (triplet, 3H, (H$_f$), J=8.35 Hz) 1.65 ppm (multiplet, 2H, (H$_e$)) 1.80 ppm (singlet, 3H, (H$_c$)) 2.65 ppm (triplet, 2H, (H$_d$), J=7.49 Hz) 3.10 ppm (triplet, 2H, (H$_a$)) 3.30 ppm (multiplet, 2H, (H$_2$)) 3.90 ppm (singlet, 3H, (OCH$_3$)) 7.10 ppm (multiplet, 2H, (H$_6$, H$_2$)) 7.50 ppm (singlet, 1H, (H$_4$)) 7.55 ppm (doublet, 1H, (H$_8$), J$_{8-6}$=1.95 Hz) 7.75 ppm (doublet, 1H, (H$_5$), J$_{5-6}$=8.39 Hz) 8.10 ppm (triplet, 1H, (NH))

EXAMPLES 144 TO 148

By working as in Examples 1, 49, 50, 115 and 120, but starting with the corresponding thiocarboxamide compounds, the compounds of the following examples are obtained:

EXAMPLE 144:

N-[2-(7-METHOXY-3-BENZOYLNAPHTH-1-YL)-ETHYL]THIOACETAMIDE

EXAMPLE 145:

N-[2-(7-METHOXY-3-ACETYLNAPHTH-1-YL)-ETHYL]THIOACETAMIDE

EXAMPLE 146:

N-[2-(7-METHOXY-3-ACETYLNAPHTH-1-YL)-ETHYL]CYCLOPROPYL THIOCARBOXAMIDE

EXAMPLE 147:

N-[2-(7-METHOXY-3-ETHYLNAPHTH-1-YL)-ETHYL]THIOACETAMIDE

EXAMPLE 148:

N-[2-(7-METHOXY-3-ETHYLNAPHTH-1-YL)-ETHYL]CYCLOPROPYLTHIOCARBOXAMIDE

PHARMACOLOGICAL STUDY OF THE DERIVATIVES OF THE INVENTION

EXAMPLE A: STUDY OF THE ACUTE TOXICITY

The acute toxicity was assessed after oral administration to batches of 8 mice (26 2 grams). The animals were observed at regular intervals in the course of the first day and daily for the two weeks following the treatment. The LD$_{50}$ causing the death of 50% of the animals was evaluated. The LD$_{50}$ of the products tested is greater than 1000 mg.kg$^{-1}$ for the compounds studied, which indicates the low toxicity of the compounds of the invention.

EXAMPLE B: FOUR PLATE TEST

The products of the invention are administered via the esophagus to batches of ten mice. One batch receives gum syrup. 30 minutes after administration of the products to be studied, the animals are placed in rooms the floor of which comprises four metal plates. Each time that the animal passes from one plate to another, it receives a mild electric shock (0.35 mA). The number of passages is recorded over one minute. After administration, the compounds of the invention significantly increase the number of passages, which shows the anxiolytic activity of the derivatives of the invention.

EXAMPLE C: ACTIVITY OF THE PRODUCTS OF THE INVENTION ON ISCHEMIC MICROCIRCULATION

The experimental study was performed on the cremaster muscles of male rats (Sprague-Dawley) after ligature of the common iliac artery.

The muscles were placed in a transparent chamber and infused with a solution of bicarbonate buffer equilibrated with a CO$_2$/N$_2$ 5/95% gaseous mixture. The speed of the red corpuscles and the diameter of the first or second order arterioles irrigating the cremaster were measured, and the arterial-blood flow was calculated. Identical information was obtained for four types of venule.

The same type of measurement was carried out simultaneously:

- on the cremaster infused normally,
- on the ligatured cremaster, that is to say the ischemic cremaster 2, 7, 14 and 21 days after ligature.

Two groups of animals were studied:

- a control group without treatment,
- a group treated orally with a product of the invention, in an amount of 0.1 mg.kg$^{-1}$ per day.

No difference was observed in the speed of the corpuscles nor in the blood vessel diameter in the cremaster muscles irrigated normally in the treated animals with respect to the control animals.

On the contrary, the mean diameter of the arterioles in the ischemic cremaster muscle was enhanced in the treated animals with respect to the control animals. The speed of the red corpuscles was standardized by a treatment for 21 days.

Indeed, in the treated animals, the speed of the red corpuscles and the blood flow measured 7 days after the ligature show no significant difference with the values obtained in the non-ischemic cremaster. These results are obtained without modification of the arterial pressure.

These results indicate that chronic treatment with a compound of the invention improves the blood irrigation and microcirculation of the ischemic regions.

EXAMPLE D: STIMULATION OF THE IMMUNE RESPONSES

Red corpuscles from sheep were administered to groups of six mice. These groups of mice were subsequently treated subcutaneously with the compounds of the invention for six days and a control group was treated with a placebo. The mice were subsequently left to rest for four weeks and then received a repeat injection of sheep red corpuscles without receiving repeat administrations of product of the invention. The immune response was evaluated 3 days after the repeat injection. It is statistically higher in the group treated with the compounds of the invention.

EXAMPLE E: EFFECTS OF THE COMPOUNDS OF THE INVENTION ON THE CIRCADIANS RHYTHMS OF LOCOMOTOR ACTIVITY

The involvment of melatonin in the entrainment, by light-dark cycle, of most of the physiological and biochemical circadian rhythms allowed to establish a pharmacological model for the search of melatoninergic ligands.

The effects of the compounds of the invention are tested on several parameters and particularly on the circadian rhythms of locomotor activity, which represent a reliable marker of the endogenous circadian clock activity.

PROTOCOL:

One-month old male Long Evans rats were subjected to a daily cycle of 12 h light/12 h darkness (LD 12: 12) for 2–3 weeks, being maintained in cages equipped with running wheels linked to a recording system in order to detect and note locomotor activity phases as well as circadian rhythms.

They are then kept under constant darkness until a stable free-running rhythm was established, and after this establishment, rats were then given daily an administration of the tested compound.

The reports are carried out with activity rhythm visualization:

activity rhythms entrainment under the daily cycle (LD 12: 12).

disparition of the rythm entrainment under constant darkness entrainment by the daily administration of the tested compound;

RESULTS:

Taken together, the results evidence the therapeutic interest of the compounds of the invention as chronobiotic for circadian rhythm disorders.

EXAMPLE F: DEMONSTRATION OF THE ANALGESIC ACTIVITY

Research into the activity on pain was performed in mice (23–25 g) according to a procedure derived from the technique described by SIEGMUND (Siegmund E. A., R. A. Cadmus & Golu, J. Pharm. Exp. Ther. 119, 1874, 1954). The mice, randomly distributed into batches of 12 animals, received the treatment orally (excipient for the controls) 1 hour before intraperitoneal injection of an aqueous-alcoholic 0.02% solution of phenyl-p-benzoquinone (Sigma). The number of stretches is counted between the 5th and 10th minute after the injection.

It is apparent that the compounds of the invention possess an analgesic activity.

EXAMPLE G: TEST OF BINDING TO THE MELATONIN RECEPTORS ON SHEEP TUBERALIS PARS

The binding of the compounds of the invention to the melatonin receptors was performed, according to the standard techniques, on sheep Pars Tuberalis, as described in "Journal of Neuroendocrinology, vol. 1, No.1, 1989".

It appears that the compounds of the invention bind very specifically to the melatonin receptors, with an affinity which is superior to that of melatonin itself.

EXAMPLE H: TEST OF COMPETITION FOR THE MELATONIN RECEPTORS ON GALLUS DOMESTICUS CHICK BRAIN CELL MEMBRANES

The animals used are 12-day-old chicks (Gallus domesticus). They are sacrificed between 1 pm and 5 pm on the day of their arrival. The brains are rapidly removed and frozen at −200° C. and then stored at −80° C. The membranes are prepared according to the method described by Yuan and Pang (1991). The binding of melatonin to the membranes is performed according to a procedure established by Rivkees et al. (1989). Briefly, [$^{125}$I]-melatonin is incubated in the presence of the membranes in a solution buffered at pH 7.4 for 60 min at 25° C. At the end of this period, the membrane suspension is filtered (Whatman GF/C). The radioactivity retained on the filter is determined using an LS 6000 Beckman® liquid scintillation counter.

The products used are:

2 [$^{125}$I]-melatonin melatonin usual materials original molecules

In the primary screening, the molecules are tested at 2 concentrations ($10^{-7}$ and $10^{-5}$ M). Each result is the average of n=3 independent measurements. The active molecules selected according to the results of the primary screening formed the subject of a quantitative determination of their effectiveness ($IC_{50}$). They are used at 10 different concentrations.

Thus, the $IC_{50}$ values found for the preferred compounds of the invention, which correspond to the values of the affinity, show that the binding of the compounds tested to the melatoninergic receptors is, surprisingly, very powerful.

EXAMPLE I: PHARMACEUTICAL COMPOSITION: TABLETS

Tablets containing a 5 mg dose of N-[2-(7-methoxy-3-ethylnaphth-1-yl)ethyl]acetamide. Formulation to prepare 1000 tablets.

N-[2-(7-methoxy-3-ethylnaphth-1-yl)ethyl]acetamide 5 g Wheat starch 15 g Corn starch 15 g Lactose 15 g Magnesium stearate 2 g Silica 1 g Hydroxypropyl cellulose 2 g

We claim:

1. A compound of formula (I):

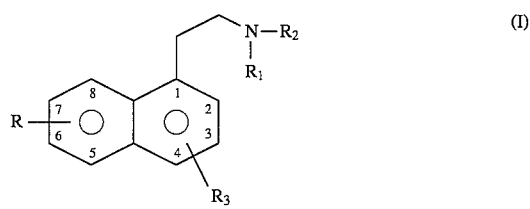

in which:

R represents hydrogen or a radical chosen from alkyl, substituted alkyl and —O—R'; with R' representing hydrogen or a radical selected from alkyl, substituted alkyl, cycloalkyl, substituted cycloalkyl, cycloalkylalkyl, substituted cycloalkylalkyl, phenyl, substituted phenyl, phenylalkyl, substituted phenylalkyl, diphenylalkyl and substituted diphenylalkyl;

$R_1$ represents hydrogen or alkyl;

$R_2$ represents a)

in which $X^1$ represents sulfur or oxygen and $R_{40}$ represents hydrogen or a radical chosen from alkyl, substituted alkyl, cycloalkyl, substituted cycloalkyl, cycloalkylalkyl, substituted cycloalkylalkyl, alkenyl, substituted alkenyl, alkynyl and substituted alkynyl;

or b)

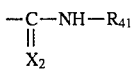

in which $X^2$ represents sulfur or oxygen and $R_{41}$ represents hydrogen or a radical chosen from alkyl, cycloalkyl and cycloalkylalkyl;

$R_3$ represents a radical chosen from:
- $(C_2-C_6)$ alkyl,
- substituted $(C_2-C_6)$ alkyl,
- cycloalkylalkyl,
- substituted cycloalkylalkyl,
- alkenyl,
- substituted alkenyl,
- alkynyl,
- substituted alkynyl,
- hydroxyl in 3-position,
- $R_5$-alkyl-, with $R_5$ being substituted or unsubstituted and representing a radical chosen from phenyl and naphthyl;
- $R_6$—CO—O—,
- and $R_6$—CO—, with $R_6$ representing a radical chosen from $(C_1-C_5)$alkyl, substituted $(C_1-C_5)$alkyl, cycloalkyl, substituted cycloalkyl, cycloalkyl$(C_1-C_5)$alkyl, substituted cycloalkyl$(C_1-C_5)$alkyl, $R_5$- and $R_5$-alkyl- where $R_5$, being unsubstituted or substituted, is as defined above, it being understood that the compound of formula (I) cannot be N-{2-[(4-acetyl)naphth-1-yl]ethyl}acetamide, wherein the terms "alkyl" and "alkoxy" denoting inclusively, except where otherwise mentioned, linear or branched groups of 1 to 6 carbon atoms, the terms "alkenyl" and "alkynyl" denoting inclusively unsaturated, linear or branched groups of 2 to 6 carbon atoms, the term "cycloalkyl" denoting inclusively a cyclic group of 3 to 8 carbon atoms, the term "substituted", applied to "alkyl", "alkoxy", "alkenyl", "alkynyl", "cycloalkyl" or "cycloalkylalkyl", means that these groups are substituted with one or more radicals chosen from alkyl, alkoxy and halogen;

the term "substituted" associated with $R_5$ and with "phenyl", "phenylalkyl" or "diphenylalkyl" means that these groups are substituted with one or more radicals chosen from alkyl, alkoxy, halogen, hydroxyl and trifluoromethyl;

their enantiomers and diastereoisomers, and their addition salts with a pharmaceutically acceptable acid or base.

2. A compound of claim 1, which is N-[2-(7-methoxy-3-benzoylnaphth-1-yl)ethyl]acetamide.

3. A compound of claim 1, which is N-[2-(7-methoxy-3-acetylnaphth-1-yl)ethyl]acetamide.

4. A compound of claim 1, which is N-[2(7-methoxy-3-acetylnaphth-1-yl)ethyl]cyclopropylcarboxamide.

5. A compound of claim 1, which is N-[2(7-methoxy-3-ethylnaphth-1-yl)ethyl]acetamide.

6. A compound of claim 1, which is N-[2(7-methoxy-3-propylnaphth-1-yl)ethyl]acetamide.

7. A compound of claim 1 which is N-[2(7-methoxy-3-hydroxynaphth-1-yl)ethyl]acetamide.

8. A compound of claim 1 which is N-[2-(7-methoxy-3-cyclopropylcarbonylnaphth-1-yl)ethyl]acetamide.

9. A compound of claim 1 which is N-[2-(7-methoxy-3-acetoxynaphth-1-yl)ethyl]acetamide.

10. A compound of claim 1 which is N-[2-(7-methoxy-3-hydroxynaphth-1-yl)ethyl]acetamide.

11. A compound of claim 1 which is N-[2-(3,7-dihydroxynaphth-1-yl)ethyl]acetamide.

12. A compound of claim 1 which N-[2-(7-methoxy-3-benzylnaphth-1-yl)ethyl]acetamide.

13. A compound of claim 1 which is N-[2-(7-methoxy-3-ethylnaphth-1-yl)ethyl]cyclopropylcarboxamide.

14. A compound of claim 1 which is N-[2-(7-methoxy-3-cyclopropylmethylnaphth-1-yl)ethyl]acetamide.

15. A pharmaceutical composition useful in treating sleep disorders containing a compound of claim 1 in combination with one or more pharmaceutically-acceptable excipients.

16. A method of treating a mammal afflicted with a disorder of the melatoninergic system comprising the step of administrating to said mammal an effective amount of a compound according to claim 1 for alleviation of said disoder.

17. A method of treating a mammal afflicted with a sleeping disorder comprising the step of administering to said mammal an effective amount of a compound according to claim 1 for alleviation of said disorder.

* * * * *

UNITED STATES PATENT AND TRADEMARK OFFICE
CERTIFICATE OF CORRECTION

PATENT NO. : 5,591,775
DATED : January 7, 1997
INVENTOR(S) : P. Depreux; H. Mansour; D. Lesieur; F. Lefoulon; P. Renard; G. Adam; P. Delagrange It is certified that error appears in the above-indentified patent and that said Letters Patent is hereby corrected as shown below:

Column 2, line 36: Delete excessive space after "alkyl," and before "substituted".

Column 10, line 16: "-11-YL)-" should read -- -1-YL)- --.

Column 22, line 28: Delete "N-" in this line.

Column 22, line 30: Insert -- N- -- at the beginning of the line.

Column 23, line 65: "-31-BENZYL" should read: -- -3-BENZYL --.

Column 24, line 42: Delete the "-" at the end of the line and insert ")".

Column 24, line 43: Delete the ")" from the beginning of the line.

Column 28, line 61: Delete the "-" at the end of the line and insert ")".

Column 28, line 62: Delete the ")" from the beginning of the line.

Column 33, line 5 (approx.): "$X_2$" in the formula should read -- $X^2$ --.

UNITED STATES PATENT AND TRADEMARK OFFICE
CERTIFICATE OF CORRECTION

PATENT NO. : 5,591,775
DATED : January 7, 1997
INVENTOR(S) : P. Depreux; H. Mansour; D. Lesieur; F. Lefoulon; P. Renard; G. Adam; P. Delagrange It is certified that error appears in the above-indentified patent and that said Letters Patent is hereby corrected as shown below:

Column 33, line 26: Delete excessive space after "alkyl," and before "substituted" in the line.

Column 34, line 4: Insert a -- - -- (dash) between "pharmaceutically" and "accept-".

Column 34, line 28(approx.): In Claim 12, insert -- is -- after "which".

Signed and Sealed this

First Day of April, 1997

BRUCE LEHMAN

*Attest:*

*Attesting Officer*    Commissioner of Patents and Trademarks